United States Patent [19]

Thenappan et al.

[11] Patent Number: 5,545,775
[45] Date of Patent: Aug. 13, 1996

[54] LIQUID PHASE PROCESS FOR THE PREPARATION OF 1,1-DIFLUOROETHANE

[75] Inventors: Alagappan Thenappan, Cheektowaga; Charles F. Swain, Williamsville; Matthew H. Luly, Lancaster, all of N.Y.

[73] Assignee: AlliedSignal Inc., Morris Township, N.J.

[21] Appl. No.: 519,446

[22] Filed: Aug. 25, 1995

[51] Int. Cl.$^6$ ............ C07C 17/093; C07C 17/20; C07C 19/08
[52] U.S. Cl. ............................. 570/168; 570/167
[58] Field of Search ............................ 570/167, 168

[56] References Cited

U.S. PATENT DOCUMENTS

| | | | |
|---|---|---|---|
| 2,452,975 | 11/1948 | Walley | 260/653 |
| 3,190,930 | 6/1965 | Brock et al. | 260/653.6 |
| 3,978,145 | 8/1976 | Knaak | 260/653.6 |
| 5,008,474 | 4/1991 | Wairaevens et al. | 570/168 |

FOREIGN PATENT DOCUMENTS

| | | |
|---|---|---|
| 832502 | 1/1970 | Canada. |
| 1069019A | 2/1993 | China. |
| 6-228021 | 8/1994 | Japan ............ 570/167 |

*Primary Examiner*—Joseph E. Evans
*Attorney, Agent, or Firm*—Lois A. Gianneschi

[57] ABSTRACT

1,1-difluoroethane is produced by the reaction of 1,2-dichloroethane with anhydrous hydrogen fluoride in a liquid phase and in the presence of a Lewis acid. Preferably the Lewis acid is tin, antimony, titanium, molybdenum, tungsten, niobium or tantalum halide or a mixture thereof.

23 Claims, No Drawings

LIQUID PHASE PROCESS FOR THE PREPARATION OF 1,1-DIFLUOROETHANE

BACKGROUND OF THE INVENTION

1. Field of the Invention

The invention pertains to the production of 1,1-difluoroethane, or more particularly to the production of 1,1-difluoroethane by the reaction of 1,2-dichloroethane with anhydrous hydrogen fluoride in a liquid phase and in the presence of a Lewis acid.

2. Description of the Prior Art

Hydrofluorocarbons or HFC's are of interest due to their potential to replace ozone depleting chlorofluorocarbons or CFC's in a variety of applications, including refrigerants, aerosol propellants, foam blowing agents and solvents. 1,1-difluoroethane, HFC-152a, has been identified as a useful aerosol propellant and a component in refrigerant blends and has no known ozone depletion potential. It is not classified as a volatile organic compound and has very low global warming potential. Therefore, HFC-152a is an ideal candidate to replace chlorofluorocarbon propellants in such consumer products as antiperspirants and hairsprays.

There are known methods for producing 1,1-difluoroethane. Japanese Kokai JP6-228021 fluorinates 1,1-dichloroethane. Canadian patent 832,502 reacts a mixture of 1,2-dichloroethane and vinyl chloride with hydrogen fluoride in a vapor phase in the presence of a chrome oxide catalyst with subsequent separation of produced vinyl fluoride and 1,1-difluoroethane. U.S. Pat. No. 2,452,975 fluorinates a polychlorinated ethane to a polyfluorinated ethane, however, at least two chlorine atoms must be attached to the same carbon atom. U.S. Pat. No. 3,978,145 fluorinates halogenated aliphatic compounds with hydrogen fluoride, however this is done in a vapor phase using a hexagonal chromium(III) oxide hydroxide. Chinese patent application 92100388.9 teaches the fluorination of chloroethylene. U.S. Pat. No. 3,190,930 prepares 1,1-difluoroethane by reacting acetylene and hydrogen fluoride. Liquid phase fluorination of 1,2-dichloroethane to give HFC-152a is not known in the art. Although the above chloroethane feeds for HFC-152a processes are commercially available, 1,1-dichloroethane is more expensive than 1,2-dichloroethane. The gas phase fluorination of 1,2-dichloroethane has several disadvantages, namely, a higher reaction temperature, formation of large quantity of vinyl chloride intermediate and poor selectivity of 1,1-difluoroethane. Vinyl chloride is carcinogenic and difficult to separate for recycling. Its propensity to polymerize in the presence of hydrogen fluoride will often lead to varying quantities of coke which leads to reduced catalyst life time. At lower temperatures(<200°0 C.), the reaction does not proceed sufficiently to give 1,1-difluoroethane and at higher reaction temperatures(>400° C.), degradation of catalyst and a mixture of vinyl chloride, vinyl fluoride and 1,1-difluoroethane are formed. Separation of this mixture to obtain pure 1,1-difluoroethane by distillation is tedious and expensive. It would therefore be advantageous to provide a process for the production of 1,1-difluoroethane by the reaction of 1,2-dichloroethane with anhydrous hydrogen fluoride in a liquid phase.

SUMMARY OF THE INVENTION

The invention provides a process for the preparation of 1,1-difluoroethane which comprises reacting 1,2-dichloroethane with at least two equivalents of anhydrous hydrogen fluoride in a liquid phase in the presence of at least one Lewis acid catalyst.

DETAILED DESCRIPTION OF THE PREFERRED EMBODIMENT

The process of the invention prepares 1,1-difluoroethane (HFC-152a) by reacting 1,2-dichloroethane (HCC-150) with anhydrous hydrogen fluoride in a liquid phase and in the presence of at least one Lewis acid catalyst. In the preferred embodiment, the process further comprises the subsequent step of separating 1,1-difluoroethane such as by distillation. In the process, the Lewis acid is preferably a tin, antimony, titanium, molybdenum, tungsten, niobium or tantalum halide including mixtures thereof. The process can be carried out in an autoclave constructed of a metal resistant to attack by the reactants, such as stainless steel, nickel, Monel, Inconel, Hastalloy-C. The autoclave may be lined with resins which are resistant to attack by the reactants such as hydrogen fluoride, catalyst, solvent and dichloroethane.

Preferably the catalyst material is a metal chloride and the most preferred metal is tin. Tin(IV) chloride is a liquid at ambient conditions and less corrosive than antimony pentachloride or other common antimony halide catalysts. The feed materials and catalysts useful in the present invention are readily commercially available.

The amount of hydrogen fluoride used should be at least twice the stoichiometric equivalent of the HCC-150 used, and it is preferable to use an excess of hydrogen fluoride. Preferably the mole ratio of hydrogen fluoride to HCC-150 ranges from about 2:1 to about 15:1, more preferably from about 10:1 to about 15:1 and most preferably from about 10:1 to about 12:1. The useful amount of catalyst ranges from about 2 to 80 weight % based on the amount of HCC-150, or more preferably from about 5% to about 20% and most preferably from about 8% to about 15%. The reaction is preferably conducted at a temperature ranging from 100° C. to about 250° C., more preferably from about 125° C. to about 150° C. and most preferably from about 140° C. to about 145° C. The pressure of the reaction varies depending on the quantity of hydrogen fluoride used and conversion of HCC-150. Pressure may be adjusted by continuously removing hydrogen chloride and HFC-152a from the reactor by distillation.

Useful residence times in the reactor range from about 1 hour to about 20 hours, preferably from about 1 hour to about 6 hours and most preferably from about 3 hours to about 6 hours. Resulting HFC-152a may be separated from the reaction mixture via any known separation and purification method known in the art such as neutralization and distillation. The process may be carried out either in a batch or continuous method. Continuous method requires the removal of volatile HFC-152a and hydrogen chloride from the reactor continuously as it is formed. Initial weight percentage of the catalyst will be higher and residence time will be shorter for a continuous process. However, substantially the same reaction temperature and pressure used in the batch process can be maintained in the continuous process when the organic feed to hydrogen fluoride ratio is kept constant.

In an alternative embodiment of the invention, the reaction may be conducted in the presence of a solvent or mixture of solvents. Suitable solvents may be polar or non-polar and are preferably saturated hydrocarbons or saturated halogenated hydrocarbons. Examples of suitable solvents non-exclusively include hydrocarbons and hydrocarbons having halogen substitutions. Examples of useful solvents include non-polar aliphatic hydrocarbon solvents non-exclusively including n-butane, isobutane, n-pentane, 2-methylbutane, n-hexane, 2-methylpentane, n-heptane and n-octane. Alicyclic hydrocarbons include cyclopentane, methylcyclopentane and cyclohexane. Fluorine substituted hydrocarbons include 1,1-difluoroethane, 1,1,1,2-tetrafluoroethane, 2,2-difluoropentane, 1,1,2-trifluoropropane, 1,1,1,2,2,3,3-heptafluoropropane, 2,2-difluorobutane, 2,2,3-trifluorobutane and perfluoroethane. Chlorine substituted hydrocarbons include 1,1,2,2-tetrachloroethane. The amount of solvent to hydrogen fluoride preferably ranges from about 0.1 to about 100 weight equivalents.

The following non-limiting examples serve to illustrate the invention.

EXAMPLE 1

The reactor used for fluorination consists of a 600 ml Monel autoclave equipped with a magnetic agitator, a pressure gauge, a liquid inlet tube and a vapor outlet line. A thermocouple measures the inside reactor temperature and the reactor is heated with a heating mantle.

3.5 g (0.0135 moles) tin(IV) chloride, 76.6 g (3.83 moles) anhydrous hydrogen fluoride and 36.2 g (0.37 moles) 1,2-dichloroethane are charged into the reactor and sealed. The mixture is then heated to 120° C. in 45 minutes and maintained at that temperature and a gauge pressure of 290 lbs/sq.inch for 30 minutes. Then the reactor temperature is increased to 144° C. in one hour and maintained at that temperature for an additional three hours with the gauge pressure of 485 psi. After the evolution of hydrogen chloride has ceased (no further pressure increase), heating is stopped and the reactor contents are released through the vapor line into a pre-evacuated and pre-cooled(−78° C.) stainless steel cylinder to give 108.6 g material. GC analysis of that material through a fluorocol column coupled with a SP-1000 at the tail end indicates the following: 1,1-difluoroethane (57.9%), 1,2-dichloroethane (33.6%), vinyl chloride (0.03%), 1-chloro-1-fluoroethane (0.7%), 1-chloro- 2-fluoroethane (2.1%), 1-chloroethane (2.7%) and high boilers (0.8%).

EXAMPLE 2

As described in Example 1, the Monel reactor is sequentially charged with 3.2 g tin(IV) chloride, 66.2 g (3.31 moles) anhydrous hydrogen fluoride and 30.5 g (0.31 moles) 1,2-dichloroethane, sealed, stirred and heated to 160° C. in 1.5 hours and maintained at that temperature for 4.5 hours with a gauge pressure of 625 psi. After the evolution of hydrogen chloride ceases, the contents of the reactor are vented as before to give 100.0 g material. GC analysis of that material using the same column indicates 1,1-difluoroethane (30.6%), 1,2-dichloroethane (46.8%), 1-chloroethane (11.2%), 1-chloro-2-fluoroethane (2.9%), and 1-chloro-1-fluoroethane (0.2%).

EXAMPLE 3

The catalyst charged in Example 2 is again used for Example 3 without any further purification or regeneration. Into the reactor containing the tin catalyst, 67.0 g (3.35 moles) anhydrous hydrogen fluoride and 30.6 g (0.31 moles) 1,2-dichloroethane are charged, sealed and the mixture is heated to 160° C. with stirring in one hour and maintained at that temperature for an additional four hours with the pressure gauge reading of 575 psi. After the evolution of hydrogen chloride has ceased, reactor contents are vented into a stainless steel cylinder to give 98.3 g material, which is analyzed by GC as 1,1-difluoroethane (41.9%), 1,2-dichloroethane (39%), 1-chloroethane (5.8%) and 1-chloro-2-fluoroethane(6.4%).

EXAMPLE 4

3.5 g (0.012 moles) antimony(V) chloride, 63.3 g (3.17 moles) anhydrous hydrogen fluoride and 35.0 g (0.35 moles) 1,2-dichloroethane are charged into the reactor of Example 1 and sealed. The mixture is then heated to 143° C. in 75 minutes and maintained at that temperature and a gauge pressure of 450 lbs/sq. inch for 4 hours. After the evolution of hydrogen chloride has ceased (no further pressure increase), heating is stopped and the reactor contents are released through the vapor line into a pre-evacuated and pre-cooled(−78° C.) stainless steel cylinder to give 94.6 g material. GC analysis of that material through a fluorocol column coupled with a SP-1000 at the tail end indicated the following: 1,1-difluoroethane (13.4%), 1,2-dichloroethane (72.6%), vinyl chloride (0%), 1-chloro-1-fluoroethane (0%) , 1-chloro-2-fluoroethane (0% ), 1-chloroethane (5.3%) and high boilers (0.7%).

What is claimed is:

1. A process for the preparation of 1,1-difluoroethane which comprises reacting 1,2-dichloroethane with at least two equivalents of anhydrous hydrogen fluoride in a liquid phase in the presence of at least one Lewis acid catalyst.

2. The process of claim 1 wherein the Lewis acid is selected from the group consisting of tin, antimony, titanium, molybdenum, tungsten, niobium and tantalum halides and mixtures thereof.

3. The process of claim 1 wherein the Lewis acid comprises tin(IV) chloride.

4. The process of claim 1 wherein the Lewis acid is present in an amount of from about 2% to about 80% based on the weight of 1,2-dichloroethane.

5. The process of claim 1 wherein the Lewis acid is present in an amount of from about 5% to about 20% based on the weight of 1,2-dichloroethane.

6. The process of claim 1 wherein the Lewis acid is present in an amount of from about 8% to about 15% based on the weight of 1,2-dichloroethane.

7. The process of claim 1 wherein the reaction is conducted at a temperature of from about 100° C. to about 250° C.

8. The process of claim 1 wherein the reaction is conducted at a temperature of from about 125° C. to about 150° C.

9. The process of claim 1 wherein the reaction is conducted at a temperature of from about 140° C. to about 145° C.

10. The process of claim 1 wherein the reaction is conducted for from about 1 hour to about 20 hours.

11. The process of claim 1 wherein the reaction is conducted for from about 1 hours to about 6 hours.

12. The process of claim 1 wherein the mole ratio of hydrogen fluoride to 1,2-dichloroethane ranges from about 2:1 to about 15:1.

13. The process of claim 1 wherein the mole ratio of hydrogen fluoride to 1,2-dichloroethane ranges from about 10:1 to about 15:1.

14. The process of claim 1 wherein the mole ratio of hydrogen fluoride to 1,2-dichloroethane ranges from about 10:1 to about 12:1.

15. The process of claim 1 wherein the Lewis acid is present in an amount of from about 2% to about 80% based on the weight of 1,2-dichloroethane; wherein the reaction is conducted at a temperature of from about 100° C. to about 250° C.; wherein the reaction is conducted for from about 1 hour to about 20 hours; wherein the mole ratio of hydrogen fluoride to 1,2-dichloroethane ranges from about 2:1 to about 15:1.

16. The process of claim 2 wherein the Lewis acid is present in an amount of from about 2% to about 80% based on the weight of 1,2-dichloroethane; wherein the reaction is conducted at a temperature of from about 100° C. to about 250° C.; wherein the reaction is conducted for from about 1 hour to about 20 hours; wherein the mole ratio of hydrogen fluoride to 1,2-dichloroethane ranges from about 2:1 to about 15:1.

17. The process of claim 1 wherein the Lewis acid is present in an amount of from about 8% to about 15% based on the weight of 1,2-dichloroethane; wherein the reaction is conducted at a temperature of from about 140° C. to about 145° C.; wherein the reaction is conducted for from about 3 hours to about 6 hours; wherein the mole ratio of hydrogen fluoride to 1,2-dichloroethane ranges from about 10:1 to about 12:1.

18. The process of claim 2 wherein the Lewis acid is present in an amount of from about 8% to about 15% based on the weight of 1,2-dichloroethane; wherein the reaction is conducted at a temperature of from about 140° C. to about 145° C.; wherein the reaction is conducted for from about 3 hours to about 6 hours; wherein the mole ratio of hydrogen fluoride to 1,2-dichloroethane ranges from about 10:1 to about 12:1.

19. The process of claim 1 wherein the Lewis acid is tin(IV) chloride and is present in an amount of from about 8% to about 15% based on the weight of 1,2-dichloroethane; wherein the reaction is conducted at a temperature of from about 140° C. to about 145° C.; wherein the reaction is conducted for from about 3 hours to about 6 hours; wherein the mole ratio of hydrogen fluoride to 1,2-dichloroethane ranges from about 10:1 to about 12:1.

20. The process of claim 1 further comprising the subsequent step of separating 1,1-difluoroethane.

21. The process of claim 1 wherein the reaction is conducted in the presence of a solvent or mixture of solvents.

22. The process of claim 21 wherein the solvent or mixture of solvents comprises one or more components selected from the group consisting of hydrocarbons and hydrocarbons having halogen substitution.

23. The process of claim 21 wherein the solvent or mixture of solvents is present in an amount of from about 0.1 to about 100 weight equivalents of solvent to hydrogen fluoride.

* * * * *